US00PP18899P2

(12) United States Plant Patent
Eskelund

(10) Patent No.: US PP18,899 P2
(45) Date of Patent: Jun. 10, 2008

(54) ROSE PLANT NAMED 'EVERA 152'

(50) Latin Name: *Rosa hybrida*
Varietal Denomination: Evera 152

(75) Inventor: Rosa Eskelund, Fåborg (DK)

(73) Assignee: Roses Forever ApS, Fåborg (DK)

( * ) Notice: Subject to any disclaimer, the term of this patent is extended or adjusted under 35 U.S.C. 154(b) by 0 days.

(21) Appl. No.: 11/700,654

(22) Filed: Jan. 30, 2007

(51) Int. Cl.
*A01H 5/00* (2006.01)

(52) U.S. Cl. ..... Plt./140

(58) Field of Classification Search ..... Plt./139, Plt./140
See application file for complete search history.

*Primary Examiner*—Annette H Para
(74) *Attorney, Agent, or Firm*—C. A. Whealy

(57) ABSTRACT

A new and distinct cultivar of Rose plant named 'Evera 152', characterized by its upright and rounded plant habit; dark green-colored leaflets; freely branching growth habit; freely flowering habit; large double red-colored flowers; flowers held upright on strong and erect peduncles; and good postproduction longevity.

1 Drawing Sheet

Botanical designation: *Rosa hybrida.*
Cultivar denomination: 'Evera 152'.

BACKGROUND OF THE INVENTION

The present Invention relates to a new and distinct cultivar of Rose plant, botanically known as *Rosa hybrida,* commercially used as a potted Rose, and hereinafter referred to by the name 'Evera 152'.

The new Rose is a product of a planned breeding program conducted by the Inventor in Fåborg, Denmark. The objective of the breeding program was to develop new potted Rose varieties with novel and attractive flower colors, disease resistance and excellent postproduction longevity.

The new cultivar originated from a cross-pollination made by the Inventor on Mar. 1, 2004 of a proprietary Rose selection identified as code number 03-0428, not patented, as the female, or seed, parent with an unnamed Rose selection, not patented, as the male, or pollen, parent. The cultivar Evera 152 was discovered and selected by the Inventor in on Jun. 20, 2004 as a single flowering plant within the progeny of the stated cross-pollination in a controlled environment in Fåborg, Denmark.

Asexual reproduction of the new Rose by cuttings at Fåborg, Denmark since Oct. 20, 2005, has shown that the unique features of this new Rose are stable and reproduced true to type in successive generations of asexual reproduction.

SUMMARY OF THE INVENTION

The following traits have been repeatedly observed and are determined to be the unique characteristics of 'Evera 152'. These characteristics in combination distinguish 'Evera 152' as a new and distinct cultivar:

1. Upright and rounded plant habit.
2. Dark green-colored leaflets.
3. Freely branching growth habit.
4. Freely flowering habit.
5. Large double red-colored flowers.
6. Flowers held upright on strong and erect peduncles.
7. Good postproduction longevity.

Plants of the new Rose differ from plants of the parent selections in the following characteristics:

1. Plants of the new Rose and the parent selections differ in plant habit.
2. Plants of the new Rose and the parent selections differ in flower color.

Plants of the new Rose can be compared to plants of the Rose cultivar Evera 117, disclosed in U.S. Plant patent Ser. No. 11/146,199. In side-by-side comparisons conducted in Fåborg, Denmark, plants of the new Rose differed from plants of the cultivar Evera 117 in the following characteristics:

1. Plants of the new Rose were more freely branching than plants of the cultivar Evera 117.
2. Plants of the new Rose had more petals per flower than plants of the cultivar Evera 117.
3. Plants of the new Rose and the cultivar Evera 117 differed in flower color.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph at the top of the sheet comprises a side perspective view of a typical plant of 'Evera 152' grown in a container.

The photograph at the bottom of the sheet is a close-up view of a typical flower of 'Evera 152'.

DETAILED BOTANICAL DESCRIPTION

The new Rose has not been observed under all possible environmental conditions. The phenotype may vary somewhat with variations in environment such as temperature and light intensity, without, however, any variance in genotype. The aforementioned photographs, following observations and measurements describe plants grown during the summer and early autumn in Fåborg, Denmark, in a glass-covered greenhouse and under commercial production practices. Plants were pinched one time and were about 12 to 14 weeks old when the photographs and description were taken. During the production of the plants, day temperatures averaged 22° C., night temperatures averaged 21° C. and light levels were about 20,000 lux. In the following description, color references are made to The Royal Horticultural Society Colour Chart, 2001 Edition, except where general terms of ordinary dictionary significance are used.

Botanical classification: *Rosa hybrida* cultivar Evera 152.

Parentage:

*Female, or seed, parent.*—Proprietary seedling selection of *Rosa hybrida* identified as code number 03-0428, not patented.

*Male, or pollen, parent.*—Unnamed selection of *Rosa hybrida,* not patented.

Propagation:

*Type.*—By cuttings.

*Time to initiate roots.*—About ten to twelve days at 24° C.

*Time to produce a rooted young plant.*—About one month at 24° C.

*Root description.*—Fibrous, medium thickness; white in color.

*Rooting habit.*—Freely branching; moderately dense.

Plant description:

*Plant form.*—Upright and rounded plant habit.

*Growth habit.*—Moderately vigorous growth habit. Freely branching habit; about two to four lateral branches develop from the pinching; dense and bushy growth habit.

*Plant height.*—About 20 cm to 27 cm.

*Plant width* (*spread*).—About 14 cm to 18 cm.

*Lateral branches.*—Length: About 14 cm to 20 cm. Diameter: About 3 mm. Internode length: About 1 cm to 2 cm. Strength: Strong. Texture: Smooth, glabrous. Color: Close to 146A. Thorns: Density: About three per linear cm. Shape: Triangular with sharp acuminate apices. Height: About 3 mm to 5 mm. Diameter, at base: About 1 mm to 2 mm. Color, immature: Close to 149D. Color, mature: Close to 161C to 161D.

Foliage description:

*Arrangement.*—Alternate; compound with three to five leaflets per leaf.

*Leaf length.*—About 8 cm to 9 cm.

*Terminal leaflet length.*—About 4.3 cm to 5 cm.

*Lateral leaflet length.*—About 2.3 cm to 3.3 cm.

*Leaf width.*—About 6.5 cm to 7 cm.

*Terminal leaflet width.*—About 2.8 cm to 3 cm.

*Lateral leaflet width.*—About 1.8 cm to 2.6 cm.

*Leaflet shape.*—Ovate.

*Leaflet apex.*—Apiculate.

*Leaflet base.*—Obtuse.

*Leaflet margin.*—Serrulate.

*Leaflet texture, upper and lower surfaces.*—Smooth, glabrous; leathery.

*Leaflet venation pattern.*—Pinnate; reticulate.

*Leaflet color.*—Developing leaflets, upper surface: Close to 137C. Developing leaflets, lower surface: Close to 147B. Fully expanded leaflets, upper surface: Darker than 147A; venation, close to 176A to 176D. Fully expanded leaflets, lower surface: Close to 191A; venation, close to 147C.

*Petioles.*—Leaf petiole length: About 1.5 cm to 2.5 cm. Leaflet petiole length: About 1 mm to 2 mm. Leaf petiole diameter: About 1 mm. Leaflet petiole diameter: About 1 mm. Leaf petiole texture, upper surface: Rough. Leaf petiole texture, lower surface: Smooth. Leaflet petiole texture, upper and lower surfaces: Smooth. Leaf and leaflet petiole color, upper surface: Close to 146A. Leaf and leaflet petiole color, lower surface: Close to 144A.

*Stipules.*—Quantity: Two per leaf. Length: About 3 mm to 5 mm. Width: About 1 mm. Shape: Lanceolate to falcate. Apex: Acuminate. Base: Truncate. Margin: Ciliate. Texture, upper and lower surfaces: Leathery. Color, upper surface: Close to 137A. Color, lower surface: Close to 137B.

Flower description:

*Flower type and habit.*—Large double red-colored flowers with numerous petals. Consistently symmetrical rosette flowers. Flowers borne singly on erect and strong peduncles; one terminal flower per lateral branch. Flowers persistent.

*Flowering season.*—Year-round under greenhouse conditions, optimal flowering from spring through autumn under garden conditions; flowering intermittent.

*Flower diameter.*—About 4 cm to 6 cm.

*Flower depth* (*height*).—About 2.5 cm to 3.5 cm.

*Flower longevity on plant.*—About two weeks.

*Fragrance.*—Moderately fragrant; typical of *Rosa.*

*Flower buds* (*at stage of showing color*).—Shape: Rounded to ovoid. Length: About 1 cm to 1.5 cm. Diameter: About 1 cm to 1.2 cm. Color: Close to 146B.

*Petals.*—Quantity: Numerous; about 125 per flower. Length: About 1.5 cm to 3.3 cm. Width: About 1 cm to 4 cm. Shape: Broadly obovate. Apex: Rounded and cuspidate. Base: Attenuate. Margin: Entire. Texture, upper and lower surfaces: Smooth, glabrous; satiny. Color: When opening, upper and lower surfaces: Brighter than 60B. Fully opened, upper surface: Darker than 53A. Fully opened, lower surface: Brighter than 58A.

*Sepals.*—Quantity per flower: Typically five. Length: About 3 cm to 3.5 cm. Width: About 7 mm to 8 mm. Shape: Linear to lanceolate. Apex: Sharply pointed. Base: Truncate. Texture, upper and lower surfaces: Pubescent. Color: When opening, upper surface: Close to 191B. When opening, lower surface: Close to 143A. Fully opened, upper surface: Close to 191A. Fully opened, lower surface: Slightly darker than 143A.

*Peduncles.*—Strength: Strong, but flexible. Aspect: Mostly erect. Length: About 3 cm to 3.5 cm. Diameter: About 2 mm to 3 mm. Texture: Rough. Color: Close to 144A.

*Reproductive organs.*—Stamens: None observed. Pistils: Quantity: About 25 to 30 per flower. Pistil length: About 3 mm to 5 mm. Stigma color: Close to 5D. Style length: About 2 mm to 3 mm. Style color: Close to 179A. Receptacle shape: Funnel-shaped. Receptacle height: About 5 mm. Receptacle diameter: About 5 mm. Receptacle texture: Smooth, glabrous. Receptacle color: Close to 144A. Seed/fruit: Seed and fruit production has not been observed.

Pathogen/pest resistance: Plants of the new Rose have not been observed to be resistant to pathogens and pests common to Roses.

It is claimed:

1. A new and distinct Rose plant named 'Evera 152' as illustrated and described.

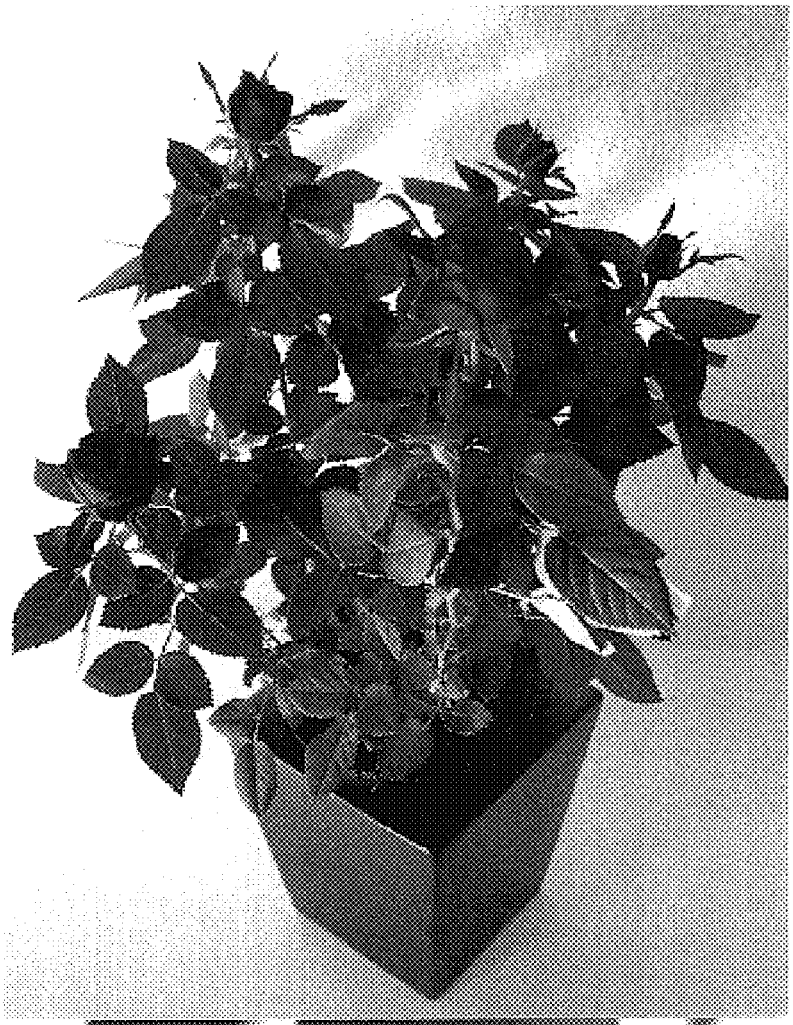
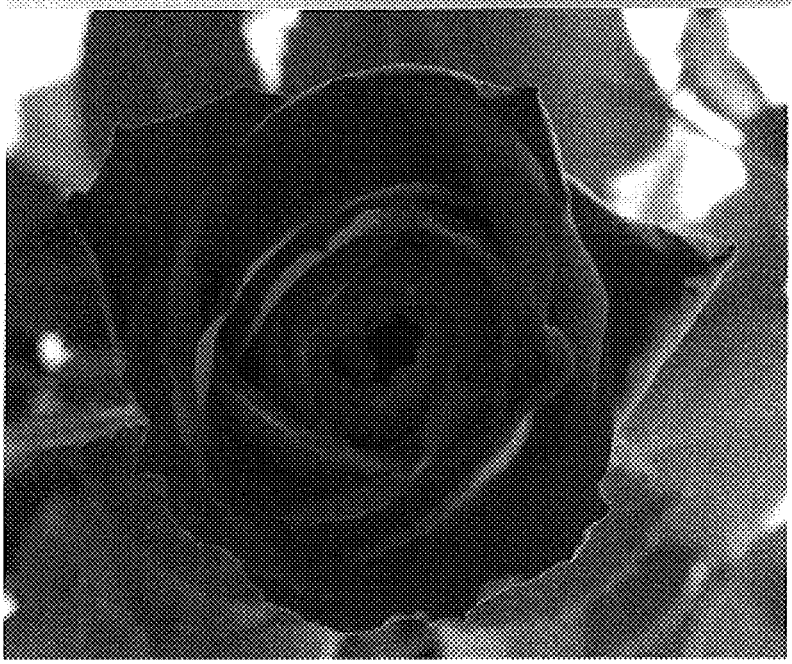

* * * * *